(12) United States Patent
Sakanishi et al.

(10) Patent No.: US 9,789,043 B2
(45) Date of Patent: Oct. 17, 2017

(54) THICKENING STABILIZER AND THICKENING/STABILIZING COMPOSITION USING THE SAME

(71) Applicants: DAICEL CORPORATION, Osaka-shi, Osaka (JP); YAMAGUCHI UNIVERSITY, Yamaguchi-shi, Yamaguchi (JP)

(72) Inventors: Yuichi Sakanishi, Ohtake (JP); Takashi Saeki, Ube (JP); Yusuke Narusaka, Ube (JP); Mami Itoh, Ube (JP)

(73) Assignees: DAICEL CORPORATION, Osaka-Shi (JP); YAMAGUCHI UNIVERSITY, Yamaguchi-Shi (JP)

( * ) Notice: Subject to any disclaimer, the term of this patent is extended or adjusted under 35 U.S.C. 154(b) by 0 days.

(21) Appl. No.: 15/101,570

(22) PCT Filed: Dec. 3, 2014

(86) PCT No.: PCT/JP2014/081976
§ 371 (c)(1),
(2) Date: Jun. 3, 2016

(87) PCT Pub. No.: WO2015/083740
PCT Pub. Date: Jun. 11, 2015

(65) Prior Publication Data
US 2016/0310384 A1    Oct. 27, 2016

(30) Foreign Application Priority Data
Dec. 6, 2013  (JP) .................................. 2013-253375

(51) Int. Cl.
C07C 233/65    (2006.01)
A61K 8/42    (2006.01)
A61Q 19/00    (2006.01)
A61K 8/92    (2006.01)

(52) U.S. Cl.
CPC .................. *A61K 8/42* (2013.01); *A61K 8/92* (2013.01); *A61Q 19/00* (2013.01); *C07C 233/65* (2013.01); *A61K 2800/48* (2013.01); *A61K 2800/52* (2013.01)

(58) Field of Classification Search
CPC .. A61K 2800/48; C07C 233/64; C07C 233/65
See application file for complete search history.

(56) References Cited

U.S. PATENT DOCUMENTS

| 2,937,203 | A | * | 5/1960 | Fuller | ................... C07C 233/12 106/10 |
| 2006/0276676 | A1 | | 12/2006 | van Bommel et al. | |
| 2013/0085087 | A1 | | 4/2013 | Mesher et al. | |
| 2014/0142004 | A1 | * | 5/2014 | Mesher | ................. C09K 8/035 507/130 |
| 2015/0376119 | A1 | | 12/2015 | Sakanishi et al. | |

FOREIGN PATENT DOCUMENTS

| EP | 1 682 491 | | 7/2006 |
| EP | 2 254 126 A1 | | 11/2010 |
| EP | 2 758 483 | | 7/2014 |
| JP | 1-163111 A | | 6/1989 |
| JP | 10231465 A | * | 9/1998 |
| JP | 2007-510791 A | | 4/2007 |
| JP | 2010-272524 A | | 12/2010 |
| JP | 2012-077195 A | | 4/2012 |
| WO | WO 2005/047231 A1 | | 5/2005 |
| WO | WO 2013/040718 A1 | | 3/2013 |
| WO | WO 2014/123110 A1 | | 8/2014 |

OTHER PUBLICATIONS

Translation of JP 10-231465 (prepared Apr. 2017).*
Translation of JP 2010-272524 (prepared Apr. 2017).*
International Search Report (PCT/ISA/210) issued in PCT/JP2014/081976, dated Jan. 13, 2015.
Written Opinion (PCT/ISA/237) issued in PCT/JP2014/081976, dated Jan. 13, 2015.
Webb et al. "Pyromellitamide Aggregates and Their Response to Anion Stimuli," Journal of the American Chemical Society, vol. 129, No. 22, May 11, 2007, pp. 7155-7162.

* cited by examiner

*Primary Examiner* — Theodore R. West
(74) *Attorney, Agent, or Firm* — Birch, Stewart, Kolasch & Birch, LLP

(57) ABSTRACT

Provided are: a compound that thickens or gelatinizes a fluid organic substance to a desired viscosity, or uniformly stabilizes a composition containing the fluid organic substance; a thickening/stabilizing agent including the compound; a thickened/stabilized composition including the thickening/stabilizing agent and a fluid organic substance; and a method for producing a thickened/stabilized composition. The compound according to the present invention is represented by Formula (1):

$$(R^2\text{—HNOC})_{4-n}\text{—}R^1\text{—}(CONH\text{—}R^3)_n \qquad (1)$$

where $R^1$ is a group resulting from removing four hydrogen atoms from the structural formula of benzene; $R^2$ and $R^3$ are different from each other and are each independently an aliphatic hydrocarbon group having 6 or more carbon atoms; and n represents an integer of 1 to 3.

5 Claims, No Drawings

THICKENING STABILIZER AND THICKENING/STABILIZING COMPOSITION USING THE SAME

TECHNICAL FIELD

The present invention relates to a novel compound that has the property of thickening/stabilizing oils and other fluid organic substances; to a thickening/stabilizing agent including the compound; and to a thickened/stabilized composition using the thickening/stabilizing agent. The present application claims priority to Japanese Patent Application No. 2013-253375 filed to Japan Dec. 6, 2013, the entire contents of which are incorporated herein by reference.

BACKGROUND ART

Techniques for thickening/stabilizing liquids are industrially very important. For example, mayonnaise and salad dressing, which are emulsions in a metastable state, can stably maintain the emulsified state over the long term because an aqueous component is thickened/stabilized. For the thickening/stabilizing techniques, various thickening/stabilizing agents have been developed.

For example, alkyl acrylate copolymers are known as compounds that thicken/stabilize aqueous media (aqueous vehicles).

In contrast, 12-hydroxystearic acid is known as a thickening/stabilizing agent for fluid organic substances (e.g., Patent Literature (PTL) 1). The fluid organic substances are exemplified by oily media and other organic substances having fluidity. The 12-hydroxystearic acid is mainly used for waste disposal of edible oils with utilizing its gelatinizing activity. However, 12-hydroxystearic acid is unadjustable in degree of gelatinization, and the target component can only be brought into a completely solidified state or remain in a liquid state as intact. Namely, under present circumstances, there has not yet been found a compound that thickens or gelatinize a fluid organic substance to a desired viscosity.

CITATION LIST

Patent Literature

PTL 1: Japanese Unexamined Patent Application Publication (JP-A) No. H01-163111

SUMMARY OF INVENTION

Technical Problem

Accordingly, the present invention has an object to provide a compound that thickens and/or gelatinizes a fluid organic substance to a desired viscosity, or uniformly stabilizes a composition containing the fluid organic substance.

The present invention has another object to provide: a thickening/stabilizing agent containing the compound; a thickened/stabilized composition that is thickened, gelatinized, and/or stabilized by the thickening/stabilizing agent; and a method for producing the thickened/stabilized composition.

Solution to Problem

After intensive investigations to achieve the objects, the inventors of the present invention found compounds having a specific structure and found that the compounds thicken and/or gelatinize a fluid organic substance, or uniformly stabilize a composition containing the fluid organic substance, namely, the compounds eliminate or minimize sedimentation, local aggregation, and concentration of the composition and can stably maintain the uniform state of the composition. The inventors also found that, when a compound is selected from among the compounds according to the type of the fluid organic substance, the compound thickens or gelatinizes the fluid organic substance to a desired viscosity, or uniformly stabilizes a composition containing the fluid organic substance. The present invention has been made based on these findings.

Specifically, the present invention provides a compound represented by Formula (1):

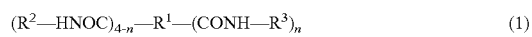

where $R^1$ is a group resulting from removing four hydrogen atoms from the structural formula of benzene; $R^2$ and $R^3$ are different from each other and are each independently an aliphatic hydrocarbon group having 6 or more carbon atoms; and n represents an integer of 1 to 3.

The present invention also provides a thickening/stabilizing agent including the compound.

The present invention also provides a thickened/stabilized composition including the thickening/stabilizing agent and a fluid organic substance.

In addition, the present invention provides a method for producing a thickened/stabilized composition. The method includes the step of dissolving the thickening/stabilizing agent and a fluid organic substance in each other.

Specifically, the present invention relates to followings.

(1) The present invention relates to a compound represented by Formula (1):

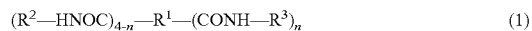

where $R^1$ is a group resulting from removing four hydrogen atoms from the structural formula of benzene; $R^2$ and $R^3$ are different from each other and are each independently an aliphatic hydrocarbon group having 6 or more carbon atoms; and n represents an integer of 1 to 3.

(2) In Formula (1) in the compound according to (1), $R^2$ may be straight or branched chain alkyl or alkenyl containing 6 to 20 (preferably 6 to 18, and particularly preferably 8 to 18) carbon atoms, and $R^3$ may be straight or branched chain alkyl or alkenyl having 6 to 20 (preferably 6 to 18, and particularly preferably 12 to 18) carbon atoms.

(3) The present invention also relates to a thickening/stabilizing agent including the compound according to one of (1) and (2).

(4) The present invention also relates to a thickened/stabilized composition including the thickening/stabilizing agent according to (3) and a fluid organic substance.

(5) The fluid organic substance in the thickened/stabilized composition according to (4) may be an organic substance having a viscosity ($\eta$) of less than 0.1 Pa·s at a temperature of 25° C. and a shear rate of 10 (1/s).

(6) The fluid organic substance in the thickened/stabilized composition according to (4) may be at least one selected from the group consisting of hydrocarbon oils, ethers, halogenated hydrocarbons, petroleum components, animal and vegetable oils, silicones, esters, aromatic carboxylic acids, and pyridine.

(7) The present invention also relates to a method for producing a thickened/stabilized composition, where the method includes the step of dissolving the thickening/stabilizing agent according to (3) and a fluid organic substance in each other.

Advantageous Effects of Invention

The compound represented by Formula (1) according to the present invention, by dissolving the compound and a fluid organic substance mutually in each other, easily thickens and/or gelatinizes the fluid organic substance, or uniformly stabilizes a composition containing the fluid organic substance. The compound, when used typically in cosmetics, coating materials, foodstuffs, and pharmaceuticals, can adjust the viscosity of these substances within a desired range, can uniformly maintain their formulations, and allows them to be used more satisfactorily.

DESCRIPTION OF EMBODIMENTS

Compound Represented by Formula (1) The compound according to the present invention is represented by Formula (1):

$$(R^2-HNOC)_{4-n}-R^1-(CONH-R^3)_n \qquad (1)$$

In Formula (1), $R^1$ is a group resulting from removing four hydrogen atoms from the structural formula of benzene; and n represents an integer of 1 to 3.

Non-limiting examples of the compound represented by Formula (1) include compounds represented by Formulae (1-1) to (1-4):

[Chem. 1]

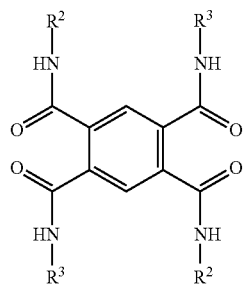

(1-1)

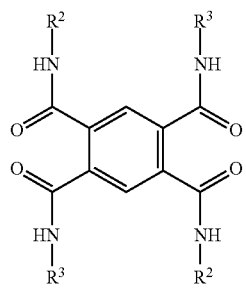

(1-2)

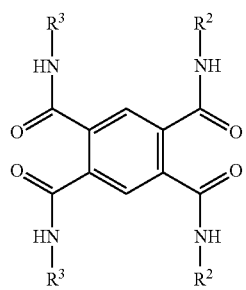

(1-3)

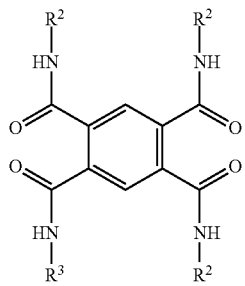

(1-4)

In particular, of the compounds represented by Formula (1) according to the present invention, preferred is at least one of the compound represented by Formula (1-1) and the compound represented by Formula (1-2). The compounds are preferred for having excellent solubility for a fluid organic substance. The compounds are preferred also because they impart a pseudoplasticity behavior and a high storage modulus to a fluid organic substance, while maintaining transparency of the fluid organic substance when the fluid organic substance is transparent.

In the formulae, $R^2$ and $R^3$ are different from each other and each represent an aliphatic hydrocarbon group having 6 or more carbon atoms. Non-limiting examples of $R^2$ and $R^3$ include straight or branched chain alkyl groups having about 6 to about 20 carbon atoms, such as hexyl, octyl, 2-ethylhexyl, decyl, lauryl, myristyl, stearyl, and nonadecyl, of which groups having 6 to 18 carbon atoms are preferred, and groups having 8 to 18 carbon atoms are particularly preferred; straight or branched chain alkenyl groups having about 6 to about 20 carbon atoms, such as 2-hexenyl, 3-hexenyl, 4-hexenyl, 5-hexenyl, 7-octenyl, 9-decenyl, 11-dodecenyl, and oleyl, of which groups having 6 to 18 carbon atoms are preferred, and groups having 12 to 18 carbon atoms are particularly preferred; and straight or branched chain alkynyl groups having about 6 to about 20 carbon atoms, such as hexynyl, octynyl, decynyl, pentadecynyl, and octadecynyl, of which groups having 6 to 18 carbon atoms are preferred, and groups having 12 to 18 carbon atoms are particularly preferred.

Of the compounds represented by Formula (1) according to the present invention, particularly preferred are compounds in which $R^2$ is branched chain alkyl having about 6 to about 20 (preferably 6 to 18, and particularly preferably 8 to 18) carbon atoms; and $R^3$ is straight chain alkyl or straight chain alkenyl each having about 6 to about 20 (preferably 6 to 18, and particularly preferably 12 to 18) carbon atoms. These compounds are preferred because they have excellent solubility for a fluid organic substance and effectively thicken the fluid organic substance.

The compounds represented by Formula (1) may be prepared typically by methods 1 and 2 as follows.

In the method 1, a benzenetetracarboxylic acid is allowed to react with thionyl chloride to give a benzenetetracarboxylic acid tetrachloride, and the resulting benzenetetracarboxylic acid tetrachloride is allowed to react with an amine (1) ($R^2$—$NH_2$) and an amine (2) ($R^3$—$NH_2$), where $R^2$ and $R^3$ are as defined above.

In the method 2, a benzenetetracarboxylic dianhydride is allowed to react with an amine (1) ($R^2$—$NH_2$) to give an amic acid, and the amic acid is further condensed with an amine (2) ($R^3$—$NH_2$) using a carbodiimide.

The benzenetetracarboxylic acid for use herein is preferably 1,2,4,5-benzenetetracarboxylic acid.

Non-limiting examples of the amines ($R^2$—$NH_2$ and $R^3$—$NH_2$) include amines containing an aliphatic hydrocarbon group having 6 or more (preferably 6 to 20) carbon atoms, such as hexylamine, octylamine, 2-ethylhexylamine, decylamine, laurylamine, myristylamine, stearylamine, and oleylamine, of which amines containing straight or branched chain alkyl, alkenyl, or alkynyl are preferred.

In the production method 1, the reaction between the benzenetetracarboxylic acid tetrachloride and the amines may be performed typically by adding the benzenetetracarboxylic acid tetrachloride dropwise to a system including the amines.

The amount of the amines (total amount of the amine (1) and the amine (2)) is typically about 4 to about 8 moles, and preferably 4 to 6 moles, per mole of the benzenetetracarboxylic acid tetrachloride.

The ratio (mole ratio) of the amine (1) to the amine (2) is adjustable as appropriate according to a desired compound represented by Formula (1). Specifically, the adjustment of the ratio of the amine (1) to the amine (2) controls the numbers of the —CONH—$R^2$ group and the —CONH—$R^3$ group in the resulting compound represented by Formula (1).

The reaction between the benzenetetracarboxylic acid tetrachloride and the amines may be performed in the presence of, or in the absence of, a solvent. Non-limiting examples of the solvent include saturated or unsaturated hydrocarbon solvents such as pentane, hexane, heptane, octane, and petroleum ether; aromatic hydrocarbon solvents such as benzene, toluene, and xylenes; halogenated hydrocarbon solvents such as methylene chloride, chloroform, 1,2-dichloroethane, chlorobenzene, and bromobenzene; ether solvents such as diethyl ether, diisopropyl ether, dibutyl ether, tetrahydrofuran, dioxane, 1,2-dimethoxyethane, and cyclopentylmethyl ether; nitrile solvents such as acetonitrile and benzonitrile; sulfoxide solvents such as dimethyl sulfoxide; sulfolane solvents such as sulfolane; amide solvents such as dimethylformamide; and high-boiling solvents such as silicone oils. Each of different solvents may be used alone or in combination.

The amount of the solvent is typically about 50% to about 300% by weight relative to the total amount of the benzenetetracarboxylic acid tetrachloride and the amines. The solvent, if used in an amount greater than the range, tends to cause the reaction to proceed at a lower reaction rate due to lower concentrations of the reaction components.

The reaction between the benzenetetracarboxylic acid tetrachloride and the amines (i.e., dropping) is generally performed under normal atmospheric pressure. The reaction atmosphere (i.e., atmosphere upon dropping) is not limited, as long as not adversely affecting the reaction, and may be selected freely from atmospheres such as air atmosphere, nitrogen atmosphere, and argon atmosphere. The reaction may be performed at a reaction temperature (i.e., temperature upon dropping) of typically about 30° C. to about 60° C. for a reaction time (i.e., dropping time) of typically about 0.5 to about 20 hours. The production method may further include an aging step after the completion of the reaction (i.e., dropping). When the production method includes the aging step, the aging may be performed at a temperature of typically about 30° C. to about 60° C. for a time of typically about 1 to about 5 hours. The reaction may be performed according to any system such as batch system, semi-batch system, or continuous system.

A reaction product after the completion of the reaction may be separated/purified by a separation process such as filtration, concentration, distillation, extraction, crystallization, adsorption, recrystallization, or column chromatography, or by a separation process as any combination of them.

In the production method 2, the compound represented by Formula (1) may be produced typically by charging the benzenetetracarboxylic dianhydride, the amine (1) ($R^2$—$NH_2$), and an after-mentioned solvent into the system and aging them to give an amic acid, thereafter charging the amine (2) ($R^3$—$NH_2$) and a condensing agent (a carbodiimide or a salt thereof) into the system and aging them.

The benzenetetracarboxylic dianhydride for use herein is preferably 1,2,4,5-benzenetetracarboxylic 1,2:4,5-dianhydride.

The amines (1) and (2) are exemplified as with the amines for use in the production method 1.

The amount of the amine (1) is typically about 2 to about 4 moles, and preferably 2 to 3 moles, per mole of the benzenetetracarboxylic dianhydride. The amount of the amine (2) is typically about 2 to about 4 moles, and preferably 2 to 3 moles, per mole of the benzenetetracarboxylic dianhydride.

The carbodiimide is represented by the formula:

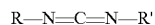

In the formula, R and R' are, for example, $C_3$-$C_8$ straight or branched chain alkyl, or 3- to 8-membered cycloalkyl, each of which may have one or more heteroatom-containing substituents. R and R' may be identical or different. R and R' may be linked to each other to form a ring with the —N=C=N— group.

Non-limiting examples of the $C_3$-$C_8$ straight or branched chain alkyl include propyl, isopropyl, butyl, isobutyl, s-butyl, t-butyl, pentyl, isopentyl, s-pentyl, t-pentyl, hexyl, isohexyl, s-hexyl, and t-hexyl.

Non-limiting examples of the 3- to 8-membered cycloalkyl include cyclopropyl, cyclobutyl, cyclopentyl, cyclohexyl, and cyclooctyl.

Non-limiting examples of the heteroatom-containing substituents include nitrogen-containing substituents such as amino, dimethylamino, and other di-($C_1$-$C_3$ alkyl)-amino.

Non-limiting examples of the carbodiimide include diisopropylcarbodiimide, dicyclohexylcarbodiimide, and N-(3-dimethylaminopropyl)-N'-ethylcarbodiimide. Non-limiting examples of the salt of the carbodiimide include hydrochlorides such as N-(3-dimethylaminopropyl)-N'-ethylcarbodiimide hydrochloride. Each of them may be used alone or in combination.

The amount of the carbodiimide is typically about 2 to about 6 moles, and preferably 2 to 4 moles, per mole of the benzenetetracarboxylic dianhydride.

The solvent is preferably selected from pyridine, triethylamine, tributylamine, and other proton-acceptor solvents that have excellent solubility for the amic acid. Each of different solvents may be used alone or in combination.

The amount of the solvent is typically about 50% to about 300% by weight, and preferably 100% to 250% by weight, relative to the total amount of the amic acid. The solvent, if used in an amount greater than the range, tends to cause the reaction to proceed at a lower reaction rate due to lower concentrations of the reaction components.

The reaction is generally performed under normal atmospheric pressure. The reaction atmosphere is not limited, as long as not adversely affecting the reaction, and may be any atmosphere such as air atmosphere, nitrogen atmosphere, or argon atmosphere. The aging (reaction) may be performed at a temperature of typically about 30° C. to about 70° C. The aging of the benzenetetracarboxylic dianhydride and the amine may be performed for a time of typically about 0.5 to about 5 hours; and the aging of the amic acid and the amine may be performed for a time of typically about 0.5 to about 20 hours. The reactions may be performed according to any system such as batch system, semi-batch system, or continuous system.

A reaction product after the completion of the reaction may be separated/purified by a separation process such as filtration, concentration, distillation, extraction, crystallization, adsorption, recrystallization, or column chromatography, or by a separation process as any combination of them.

The compound represented by Formula (1) can undergo self-association via hydrogen bonding at amide bond moieties to form a fibrous self-assembled structure. Since the groups $R^2$ and $R^3$ have affinity for a fluid organic substance, the compound, by dissolving the compound and the fluid organic substance mutually in each other, thickens and/or gelatinizes the fluid organic substance, or uniformly stabilizes a composition containing the fluid organic substance. In addition, since the groups $R^2$ and $R^3$ are different from each other, the compound represented by Formula (1) has appropriate crystallinity. This allows the compound to thicken/stabilize approximately any organic substance having fluidity without limitation. When the fluid organic substance has transparency, the compound can thicken/stabilize the fluid organic substance while maintaining the transparency and forms a thickened/stabilized composition that is stable with time. The compound is therefore useful as a thickening/stabilizing agent for fluid organic substances. More specifically, the compound is useful as any of thickeners, gelling agents, and stabilizers for fluid organic substances. In contrast, a compound represented by Formula (1) in which the groups $R^2$ and $R^3$ are identical groups (namely, a compound represented by Formula (1) having four identical groups as side chains) tends to have excessively high crystallinity and to be limited in fluid organic substances that can be thickened/stabilized by the compound. The resulting mixture which has been thickened/stabilized tends to often become cloudy and to have a poor appearance. In addition, the mixture also tends to have a decreasing viscosity with time.

Thickening/Stabilizing Agent

The thickening/stabilizing agent according to the present invention includes each of different compounds represented by Formula (1) alone or in combination.

As used herein, the term "thickening/stabilizing agent" is a concept that refers to compounds being dissolved in a fluid organic substance to develop viscosity and includes thickeners that impart viscosity to the fluid organic substance; gelling agents that gelatinize the fluid organic substance; and stabilizers that increase the viscosity of a composition containing the fluid organic substance so as to uniformly stabilize the composition.

The thickening/stabilizing agent according to the present invention may further contain one or more other components as needed, in addition to the compounds represented by Formula (1). Non-limiting examples of the other components include vehicles, hydroxy-fatty acids, acrylic polymers, dextrin fatty acid esters and other oligomer esters, and metal oxides and other particles. The content of the other components may fall within such a range that the thickening/stabilizing agent contains the compound represented by Formula (1) in a content of typically 0.5% by weight or more, preferably 1% by weight or more, more preferably 10% by weight or more, furthermore preferably 30% by weight or more, particularly preferably 60% by weight or more, and most preferably 85% by weight or more, based on the total amount (100% by weight) of the thickening/stabilizing agent. When the thickening/stabilizing agent contains two or more different compounds represented by Formula (1), the term "content" refers to the total content of them. The upper limit of the content of the compound represented by Formula (1) is 100% by weight. The thickening/stabilizing agent, if containing the compound represented by Formula (1) in a content out of the range, tends to hardly thicken and/or gelatinize the fluid organic substance, or tends to hardly stabilize a composition containing the fluid organic substance uniformly.

The dosage form of the thickening/stabilizing agent according to the present invention may be selected from various dosage forms such as powder, granule, liquid, and milky lotion forms.

Assume that the thickening/stabilizing agent according to the present invention and a fluid organic substance are dissolved mutually in each other (preferably the thickening/stabilizing agent is mixed with the fluid organic substance and heated to dissolve them in each other, and is cooled). The thickening/stabilizing agent in this case can thicken and/or gelatinize the fluid organic substance and allows, by thickening/gelatinizing, the fluid organic substance to have a desired viscosity according to the intended use, within the range of typically from greater than about 1 time to about 10000 times, preferably from greater than 1 time to 600 times, and particularly preferably from 5 to 600 times.

Thickened/Stabilized Composition

The thickened/stabilized composition according to the present invention is a composition that includes the thickening/stabilizing agent and a fluid organic substance, in which the fluid organic substance is thickened/gelatinized by the thickening/stabilizing agent, or the composition itself is uniformly stabilized by the thickening/stabilizing agent.

The thickened/stabilized composition may be produced via the step of dissolving the thickening/stabilizing agent and the fluid organic substance in each other. More specifically, the thickened/stabilized composition may be produced by mixing the total quantity of the fluid organic substance with the thickening/stabilizing agent, heating the mixture to dissolve the two components in each other, and cooling the resulting mixture. The thickened/stabilized composition may also be produced by mixing the thickening/stabilizing agent with part of the fluid organic substance, heating the mixture to dissolve the two components in each other, and cooling the resulting mixture to give a thickened/stabilized composition, and mixing the thickened/stabilized composition with the remainder of the fluid organic substance.

The fluid organic substance serving as a starting material is an organic substance having a viscosity of less than 0.1 Pa·s, where the viscosity is a viscosity ($\eta$) measured at a temperature of 25° C. and a shear rate of 10 (1/s) using a rheometer. Non-limiting examples of the fluid organic substance include hydrocarbon oils such as hexane, cyclohexane, isododecane, benzene, toluene, poly($\alpha$-olefin)s, and liquid paraffin; ethers such as tetrahydrofuran; halogenated hydrocarbons such as carbon tetrachloride and chlorobenzene; petroleum components such as kerosene, gasoline (petrol), light oil, and heavy oil; animal and vegetable oils such as sunflower oil, olive oil, soybean oil, corn oil, castor oil, beef tallow, jojoba oil, and squalane; silicones such as dimethylpolysiloxanes and methylphenylpolysiloxanes; esters such as octyldodecyl oleate, cetyl octanoate, cetyl ethylhexanoate, glyceryl triisooctanoate, and neopentyl glycol diisooctanoate; aromatic carboxylic acids; and pyridine. Each of different fluid organic substances may be used alone or in combination.

The blending amount (or amount to be used) of the thickening/stabilizing agent may vary depending on the type of the fluid organic substance, but is typically 0.1 to 100 parts by weight, preferably 0.5 to 90 parts by weight, particularly preferably 1 to 80 parts by weight, and most preferably 1 to 30 parts by weight, per 1000 parts by weight of the fluid organic substance. The thickening/stabilizing agent, when mixed (or used) in an amount within the range, can give a composition in which the fluid organic substance is thickened or gelatinized, or can give a composition whose formulation is uniformly stabilized.

The thickened/stabilized composition according to the present invention may further contain one or more other components within ranges not adversely affecting the advantageous effects of the present invention, in addition to the thickening/stabilizing agent and the fluid organic substance. The other components may be selected from medicinal components, pigments, flavors, and any other regular components to be contained in compositions that require thickening/stabilizing, such as cosmetics, coating materials, foodstuffs, and pharmaceuticals.

The temperature upon mutual dissolution may be selected as appropriate according to the types of the thickening/stabilizing agent and the fluid organic substance to be used, is not limited as long as being such a temperature that the thickening/stabilizing agent and the fluid organic substance are dissolved in each other. The temperature is, however, preferably not higher than 100° C. When the fluid organic substance has a boiling point of 100° C. or lower, the temperature is preferably around the boiling point.

The cooling after the mutual dissolution (blending) may be performed in any manner, as long as the resulting composition can be cooled down to room temperature (e.g., 25° C. or lower). The composition may be allowed to stand to cool at room temperature, or may be rapidly cooled typically by ice cooling.

The viscosity of the thickened/stabilized composition according to the present invention can be adjusted as appropriate according to the intended use, within the range of typically from greater than about 1 time to about 10000 times, preferably from greater than 1 time to 600 times, and particularly preferably from 5 to 600 times the viscosity of the fluid organic substance serving as the starting material, where the viscosity is a viscosity ($\eta$) as measured at a temperature of 25° C. and a shear rate of 10 (1/s) using a rheometer.

The thickened/stabilized composition according to the present invention is not limited, as long as the composition is a composition containing a fluid organic substance and requires being thickened/stabilized, and may be selected typically from cosmetics, coating materials, foodstuffs, and pharmaceuticals.

EXAMPLES

The present invention will be illustrated in further detail with reference to several examples below. It should be noted, however, that the examples are by no means intended to limit the scope of the present invention.

Synthesis Example 1

Synthesis of Thickening/Stabilizing Agent (1)
(1,2,4,5-benzenetetracarboxylic acid
di-2-ethylhexylamide dioleylamide)

Into a 100-mL four-neck separable flask equipped with a Dimroth condenser, a nitrogen inlet, a dropping funnel, and a thermocouple, 20 mL of pyridine, 3.0 g (0.014 mol) of 1,2,4,5-benzenetetracarboxylic 1,2:4,5-dianhydride, and 7.4 g (0.028 mol) of oleylamine were charged. The system internal temperature was set at 50° C., followed by aging for 3 hours.

Subsequently 3.6 g (0.028 mol) of 2-ethylhexylamine and 7.0 g (0.056 mol) of diisopropylcarbodiimide were charged, followed by aging for further 8 hours to give a crude mixture.

The crude mixture, from which low-boiling components were removed on an evaporator, was washed with methanol and yielded a pale yellow wet powder. Further, the obtained wet powder was recrystallized from $CHCl_3/CH_3OH$ (70/30 (v/v)) and yielded 5.9 g of 1,2,4,5-benzenetetracarboxylic acid di-2-ethylhexylamide dioleylamide in a yield of 51%, as a mixture of 1,2,4,5-benzenetetracarboxylic acid 1,4-di-(2-ethylhexylamide)-2,5-di-(oleylamide) and 1,2,4,5-benzenetetracarboxylic acid 1,5-di-(2-ethylhexylamide)-2,4-di-(oleylamide). The reaction product was identified in structure by $^1$H-NMR.

$^1$H-NMR (270 MHz, $CDCl_3$): δ 0.81-1.02 (m, 18H), 1.03-1.85 (m, 74H), 1.96-2.04 (m, 8H), 3.25-3.40 (m, 4H), 5.22-5.51 (m, 4H), 8.5-9.5 (m,2H)

FAB-MS m/z: 973 (Calcd for $C_{62}H_{110}N_4O_4$: 974)

Synthesis Example 2

Synthesis of Thickening/Stabilizing Agent (2)
(1,2,4,5-benzenetetracarboxylic acid
di-2-ethylhexylamide distearylamide))

Into a 100-mL four-neck separable flask equipped with a Dimroth condenser, a nitrogen inlet, a dropping funnel, and a thermocouple, 20 mL of pyridine, 3.0 g (0.014 mol) of 1,2,4,5-benzenetetracarboxylic 1,2:4,5-dianhydride, and 7.5 g (0.028 mol) of stearylamine were charged. The system internal temperature was set at 50° C., followed by aging for 3 hours.

Subsequently 3.6 g (0.028 mol) of 2-ethylhexylamine and 7.0 g (0.056 mol) of diisopropylcarbodiimide were charged, followed by aging for further 8 hours to give a crude mixture.

The crude mixture, from which low-boiling components were removed on an evaporator, was washed with methanol and yielded a pale yellow wet powder. Further, the obtained wet powder was recrystallized from $CHCl_3/CH_3OH$ (70/30 (v/v)) and yielded 5.1 g of 1,2,4,5-benzenetetracarboxylic acid di-2-ethylhexylamide distearylamide in a yield of 53%, as a mixture of 1,2,4,5-benzenetetracarboxylic acid 1,4-di-(2-ethylhexylamide)-2,5-di-(stearylamide) and 1,2,4,5-benzenetetracarboxylic acid 1,5-di-(2-ethylhexylamide)-2,4-di-(stearylamide). The reaction product was identified in structure by $^1$H-NMR.

$^1$H-NMR (270 MHz, $CDCl_3$): δ 0.81-1.10 (m, 18H), 1.10-1.94 (m, 90H), 3.25-3.40 (m, 4H), 8.5-9.5 (m, 2H)

FAB-MS m/z: 977 (Calcd for $C_{62}H_{114}N_4O_4$: 978)

Synthesis Example 3

Synthesis of Thickening/Stabilizing Agent (3)
(1,2,4,5-benzenetetracarboxylic acid
di-2-ethylhexylamide dilaurylamide))

Into a 100-mL four-neck separable flask equipped with a Dimroth condenser, a nitrogen inlet, a dropping funnel, and a thermocouple, 20 mL of pyridine, 3.0 g (0.014 mol) of 1,2,4,5-benzenetetracarboxylic 1,2:4,5-dianhydride, and 5.1 g (0.028 mol) of laurylamine were charged. The system internal temperature was set at 50° C., followed by aging for 3 hours.

Subsequently 3.6 g (0.028 mol) of 2-ethylhexylamine and 7.0 g (0.056 mol) of diisopropylcarbodiimide were charged, followed by aging for further 8 hours.

The crude mixture, from which low-boiling components were removed on an evaporator, was washed with methanol and yielded a pale yellow wet powder. Further, the obtained wet powder was recrystallized from $CHCl_3/CH_3OH$ (70/30 (v/v)) and yielded 6.0 g of 1,2,4,5-benzenetetracarboxylic acid di-2-ethylhexylamide dilaurylamide in a yield of 62%, as a mixture of 1,2,4,5-benzenetetracarboxylic acid 1,4-di-(2-ethylhexylamide)-2,5-di-(laurylamide) and 1,2,4,5-benzenetetracarboxylic acid 1,5-di-(2-ethylhexylamide)-2,4-di-(laurylamide). The reaction product was identified in structure by $^1$H-NMR.

$^1$H-NMR (270 MHz, $CDCl_3$): δ 0.34-1.0 (m, 18H), 1.0-2.0 (m, 66H), 2.90-3.40 (m, 4H), 8.5-9.5 (m, 2H)

FAB-MS m/z: 810 (Calcd for $C_{50}H_{90}N_4O_4$: 810)

Synthesis Example 4

Synthesis of Thickening/Stabilizing agent (4) (1,2,4,5-benzenetetracarboxylic acid tetra-(2-ethylhexylamide)

Into a 100-mL four-neck separable flask equipped with a Dimroth condenser, a nitrogen inlet, a dropping funnel, and a thermocouple, 20 mL of chloroform and 4.8 g (0.036 mol) of 2-ethylhexylamine were charged. The system internal temperature was set at 40° C.

Subsequently a solution of 3 g (0.009 mol) of pyromellitic acid tetrachloride in 10 mL of chloroform was added dropwise over 2 hours, followed by aging for further 2 hours to give a crude mixture.

The crude mixture, from which low-boiling components were removed on an evaporator, was washed with methanol and yielded a white wet powder. Further, the obtained wet powder was recrystallized from $CHCl_3/CH_3OH$ (70/30 (v/v)) and yielded 3.7 g of 1,2,4,5-benzenetetracarboxylic acid tetra-2-ethylhexylamide in a yield of 59%. The reaction product was identified in structure by $^1$H-NMR.

$^1$H-NMR (270 MHz, $CDCl_3$): δ 0.81-1.01 (m, 24H), 1.21-1.83 (m, 40H), 3.25-3.40 (m, 4H), 8.5-9.5 (m, 2H)

Synthesis Example 5

Synthesis of Thickening/Stabilizing Agent (5) (1,2,4,5-benzenetetracarboxylic acid tetraoleylamide)

Into a 100-mL four-neck separable flask equipped with a Dimroth condenser, a nitrogen inlet, a dropping funnel, and a thermocouple, 20 mL of chloroform and 9.8 g (0.036 mol) of oleylamine were charged. The system internal temperature was set at 40° C.

Subsequently a solution of 3 g (0.009 mol) of pyromellitic acid tetrachloride in 10 mL of chloroform was added dropwise over 2 hours, followed by aging for further 2 hours.

The crude mixture, from which low-boiling components were removed on an evaporator, was washed with methanol and yielded a white wet powder. Further, the obtained wet powder was recrystallized from $CHCl_3/CH_3OH$ (70/30 (v/v)) and yielded 6.4 g of 1,2,4,5-benzenetetracarboxylic acid tetraoleylamide in a yield of 56%. The reaction product was identified in structure by $^1$H-NMR.

$^1$H-NMR (270 MHz, $CDCl_3$): δ 0.81-0.95 (m, 12H), 1.03-1.85 (m, 88H), 1.96-2.04 (m, 8H), 3.12-3.40 (m, 4H), 5.35-5.56 (m, 8H), 8.7-9.1 (m, 2H)

Examples 1 to 3 and Comparative Examples 1 and 2

One cubic centimeter (1 $cm^3$) of each of fluid organic substances (liquid paraffin, isododecane, and cetyl octanoate, each having a boiling point of 100° C. or higher) given in Table 1 was weighed in a test tube, combined and mixed with 10 mg of each of the thickening/stabilizing agents prepared in the synthesis examples, stirred with heating at 100° C. to dissolve the fluid organic substance and the thickening/stabilizing agent in each other, cooled down to 25° C., and yielded a series of thickened/stabilized compositions.

The viscosities of the prepared thickened/stabilized compositions were measured, and how many times the viscosities of the fluid organic substances were increased was determined, and the thickening effect was evaluated according to criteria as follows.

Criteria

1: from greater than 1.0 time to 2.0 times

2: from greater than 2.0 times to 4.8 times

3: from greater than 4.8 times to 10 times

4: from greater than 10 times to 50 times

5: from greater than 50 times to 100 times

6: from greater than 100 times to 10000 times

The viscosities of the fluid organic materials and the thickened/stabilized compositions were measured and determined each in the following manner. The measurement was performed using a viscosity/visco-elastometer (rheometer) (HAAKE RheoStress 600 (trade name)) equipped with a cone-and-plate sensor and a Peltier temperature controller. The cone-and-plate system in the sensor used had a diameter of 60 mm with a cone angle of 1°, or a diameter of 35 mm with a cone angle of 1°, 2°, or 4°. The viscosities were measured in a steady flow viscosity measurement mode at 25° C. and at different shear rates varying in a log scale from 0.001 to 100 (1/s), based on which a viscosity curve was plotted. A viscosity at a shear rate of 10 (1/s) was determined from the viscosity curve, and this was defined as the viscosity in the present invention. Each plot employed values obtained at the time point when the torque value variation of the instrument was settled within the range of 5% and the data became stable.

The results are summarized in the following table.

TABLE 1

| | | Example 1 Thickening/ stabilizing agent (1) | Example 2 Thickening/ stabilizing agent (2) | Example 3 Thickening/ stabilizing agent (3) | Comparative Example 1 Thickening/ stabilizing agent (4) | Comparative Example 2 Thickening/ stabilizing agent (5) |
|---|---|---|---|---|---|---|
| Fluid organic | Liquid paraffin | 4 | 4 | 4 | 1 | 1 |
| | Isododecane | 6 | 6 | 6 | 1 | 2 |

TABLE 1-continued

|  | Example 1 Thickening/ stabilizing agent (1) | Example 2 Thickening/ stabilizing agent (2) | Example 3 Thickening/ stabilizing agent (3) | Comparative Example 1 Thickening/ stabilizing agent (4) | Comparative Example 2 Thickening/ stabilizing agent (5) |
|---|---|---|---|---|---|
| substance Cetyl octanoate | 6 | 6 | 6 | 1 | 1 |
| Thickening effect | Good | Good | Good | Poor | Poor |

Table 1 demonstrates that the thickening/stabilizing agents according to the present invention effectively thicken the fluid organic substances. In contrast, the thickening/stabilizing agents prepared according to the comparative examples have poor effects for thickening the fluid organic substances.

INDUSTRIAL APPLICABILITY

The compounds represented by Formula (1) according to the present invention, when dissolved mutually in or blended with a fluid organic substance, easily thicken and/or gelatinize the fluid organic substance, or uniformly stabilize a composition containing the fluid organic substance. The compounds, when used typically in cosmetics, coating materials, foodstuffs, and pharmaceuticals, therefore adjust their viscosities within desired ranges, uniformly maintain their formulations, and allow them to be used more satisfactorily.

The invention claimed is:

1. A compound of Formula (1-1) or Formula (1-2):

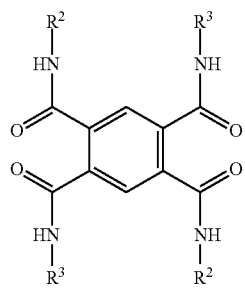

(1-1)

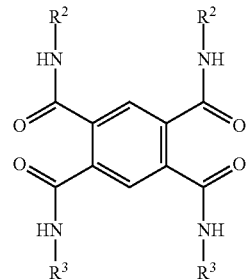

(1-2)

wherein $R^2$ and $R^3$ are different from each other and are each independently an aliphatic hydrocarbon group having 6 or more carbon atoms.

2. The compound of claim 1, wherein $R^2$ is branched chain alkyl having 6 to 20 carbon atoms and $R^3$ is straight chain alkyl having 6 to 20 carbon atoms or straight chain alkenyl having 6 to 20 carbon atoms.

3. A thickening/stabilizing agent comprising the compound according to claim 1.

4. A thickened/stabilized composition comprising:
   the thickening/stabilizing agent according to claim 3; and
   a fluid organic substance.

5. A method for producing a thickened/stabilized composition, the method comprising the step of
   dissolving the thickening/stabilizing agent according to claim 3 and a fluid organic substance in each other.

* * * * *